United States Patent
Oka et al.

(10) Patent No.: US 6,924,378 B2
(45) Date of Patent: Aug. 2, 2005

(54) METHOD FOR PRODUCTION OF AZIRIDINES AND N-VINYLAMIDES

(75) Inventors: Yoshihisa Oka, Chigasaki (JP); Kenichi Takematsu, Yokohama (JP)

(73) Assignee: Nippon Shokubai Co., Ltd., Osaka (JP)

( * ) Notice: Subject to any disclaimer, the term of this patent is extended or adjusted under 35 U.S.C. 154(b) by 202 days.

(21) Appl. No.: 10/411,502

(22) Filed: Apr. 10, 2003

(65) Prior Publication Data

US 2003/0204098 A1 Oct. 30, 2003

(30) Foreign Application Priority Data

Apr. 24, 2002 (JP) ........................................ 2002-122511

(51) Int. Cl.⁷ ............................................. C07D 203/04
(52) U.S. Cl. ....................................................... 548/954
(58) Field of Search .......................................... 548/954

(56) References Cited

U.S. PATENT DOCUMENTS 4,833,248 A * 5/1989 Shimasaki et al. .......... 546/184
4,966,980 A * 10/1990 Kamei et al. ................ 548/954
4,977,118 A * 12/1990 Tsuneki et al. ............... 502/35
5,120,860 A * 6/1992 Olson et al. ................. 548/954
6,566,534 B2 * 5/2003 Oka et al. .................... 548/954

FOREIGN PATENT DOCUMENTS

| JP | 4-217659 | 8/1992 |
| JP | 5-55498 | 8/1993 |

* cited by examiner

*Primary Examiner*—Golam M M Shameem
(74) *Attorney, Agent, or Firm*—Fish & Richardson P.C.

(57) ABSTRACT

In the production of aziridines or N-vinyl amides respectively from an alkanolamine or an alkanolamide by the known method comprising a reaction step, a collecting step and/or a condensation step, a purifying step, and a recovering step, this invention is directed toward preventing formation of a solid substance in the vacuum pumps and the vacuum lines. The object of this invention is accomplished by performing the decompression at the purifying step and the decompression at the recovering step in mutually different decompression systems.

1 Claim, 1 Drawing Sheet

(COLLECTING STEP) or (CONDENSATION STEP)　　(PURIFYING STEP)　　(RECOVERYING STEP)

US 6,924,378 B2

METHOD FOR PRODUCTION OF AZIRIDINES AND N-VINYLAMIDES

CLAIM OF PRIORITY

Under 35 USC 119, this application claims the benefit of a foreign priority application filed in Japan, serial number 2002-122511, filed on Apr. 24, 2002.

BACKGROUND OF THE INVENTION

1. Field of the Invention

This invention relates to a method for the production of aziridines and N-vinyl amides. More particularly, this invention, in the production of aziridines and N-vinyl amides by the gas phase intramolecular dehydration respectively of an alkanolamine and an alkanolamide, relates to a method for producing the aziridines and the N-vinyl amides industrially advantageously by preventing a solid substance from forming and depositing in the decompressing system which is connected to the purifying step (vacuum distillation).

2. Description of the Related Art

Aziridines are cyclic amines that have an amino group of high reactivity. The aziridine compounds are widely known compounds in the industrial world as raw materials for medicines and agricultural chemicals and as raw materials for amine type polymers used as fiber processing agents and paper processing agents. Similarly, the N-vinyl amides are very useful compounds that are widely known in the industrial world as raw materials for medicines and agricultural chemicals.

It is well known that aziridines are produced by the gas phase intramolecular dehydration (hereinafter occasionally referred to as "dehydration reaction") of alkanolamines. JP-A-04-217659, for example, discloses a method for the production of an aziridine, which comprises a step for forming an aziridine by the dehydration reaction of an alkanolamine, a step for collecting the produced aziridine by causing a reaction mixture containing the formed aziridine to contact the alkanolamine (collecting agent) used in the previous step, a step for purifying the aziridine by introducing the collected liquid containing the aziridine into a distillation column, and a step for recovering the alkanolamine in the collecting agent by introducing the bottom liquid occurring in the step of purification into the distillation column and distilling the bottom liquid in the presence of water. A similar technique is disclosed in U.S. Pat. No. 4,966,980.

By the dehydrating reaction of an alkanolamine, not only an aziridine is formed as the target product but also such amines as ammonia, methyl amine, and ethyl amine and such carbonyl compounds as acetaldehyde and acetone are formed as by-products. The by-produced carbonyl compounds may react with the aziridine, which is the target product, and form Schiff bases and ketimines. When the reaction mixture is subjected in its unaltered form to purification by distillation, therefore, the yield of the purification of an aziridine is unduly low. In the method of JP-A-04-217659, the reaction mixture containing the aziridines is brought into contact with the alkanolamine as the collecting agent so as to enable the carbonyl compound to react with the alkanolamine and undergo conversion into the Schiff bases and ketimines. Thereafter, the reaction mixture is distilled to separate amines and purify aziridines. The bottom liquid that occurs during the step of purification is distilled in the presence of water. The Schiff bases and the ketimines are decomposed into alkanolamines and carbonyl compounds and the alkanolamines are recovered.

Since the step of purification and the step of recovery are both carried out under reduced pressure, amines are extracted through the top of the distillation column at the step of purification and carbonyl compounds are extracted through the top of the distillation column at the step of recovery.

The present inventors have discovered that when the method disclosed in JP-A-04-217659 is carried out industrially, it can impose the following problems. When a single vacuum pump is used to decompress different distillation columns, amines and carbonyl compounds react inside vacuum lines and vacuum pumps that extend from the tops of the distillation columns. By this reaction, such solid substances as Schiff bases and ketimines are formed and these solid substances are suffered to clog the vacuum lines and the vacuum pumps. As a result, the control of pressure is rendered difficult and the operation of distillation is not allowed to proceed with stability. For the purpose of removing such clogging substances, it is necessary to stop the plant and wash the vacuum lines and the vacuum pumps. The efforts incur an economic burden and lower the productivity of the plant.

The problems mentioned above are not limited to the case of producing aziridines by the dehydrating reaction of alkanolamines but may occur similarly in the case of producing N-vinyl amides by the dehydrating reaction of alkanolamides. When alkanolamides are used as the raw materials, such amines as piperazine and alkyl piperazines, such aldehydes and ketones as propion aldehyde, methyl ethyl ketone, and N-butyl aldehyde are by-produced in addition to the N-vinyl amides as target products. When one and the same vacuum pump is used for the step of purification and the step of recovery, therefore, such solid substances as Schiff bases and ketimines are formed in the vacuum pumps and the vacuum lines similarly to the case of producing aziridines.

An object of this invention is to solve the problems mentioned above and provide a method for industrially advantageously producing aziridines by the dehydration reaction of an alkanolamine.

Another object of this invention is to provide a method for industrially advantageously producing N-vinyl amides by the dehydration reaction of an alkanolamide.

SUMMARY OF THE INVENTION

The present inventors, as a result of their study, have found that in a method for the production of aziridines or N-vinyl amides through the known reaction step, collecting step and/or condensation step, purifying step, and recovering step, the objects mentioned above can be accomplished by performing the vacuum distillations at the purifying step and the recovering step by the use of mutually different decompression systems. This invention has been perfected on the basis of this knowledge.

Specifically, this invention concerns a method for the production of aziridine, which comprises a reaction step for obtaining a reaction gas containing aziridine by the gas phase intramolecular dehydration of an alkanolamine, a collecting step for obtaining a collection liquid containing aziridine by causing the reaction gas to contact a collecting agent and/or a condensation step for obtaining a condensed liquid containing aziridine by cooling the reaction gas, a purifying step for obtaining purified aziridine by introducing the collection liquid and/or the condensed liquid into a distillation column and subjecting the collection liquid and/or the condensed liquid to vacuum distillation therein, and a recovering step for recovering the alkanolamine by introducing the bottom liquid in the distillation column at the purifying step into a distillation column and subjecting the bottom liquid to vacuum distillation therein, and the decompression at the purifying step and the decompression at the recovering step are carried out with mutually different decompression systems.

This invention also concerns a method for the production of N-vinyl amide, which comprises a reaction step for obtaining a reaction gas containing N-vinyl amide by the gas phase intramolecular dehydration of an alkanolamide, a collecting step for obtaining a collection liquid containing N-vinyl amide by causing the reaction gas to contact a collecting agent and/or a condensation step for obtaining a condensed liquid containing N-vinyl amide by cooling the reaction gas, a purifying step for obtaining purified N-vinyl amide by introducing the collection liquid and/or the condensed liquid into a distillation column and subjecting the collection liquid and/or the condensed liquid to vacuum distillation therein, and a recovering step for recovering the alkanolamide by introducing the bottom liquid in the distillation column at the purifying step into a distillation column and subjecting the bottom liquid to vacuum distillation therein, and the decompression at the purifying step and the decompression at the recovering step are carried out with mutually different decompression systems.

According to the method of this invention, the aziridines or the N-vinyl amides can be produced industrially advantageously by preventing the formation and deposition of a solid substance in vacuum pumps and vacuum lines.

In the method for the production of aziridines and N-vinyl amides mentioned above, any compound which is capable of collecting the formed aziridines or N-vinyl amides and reacting with the by-produced carbonyl compounds to form Schiff bases or ketimines can be used as the collection liquid. Among them, alkanolamine or alkanolamide are used particularly advantageously. They may be the same as the raw materials or different from the raw materials. Preferably they are identical with the raw materials. In the following description, this invention will be explained in detail on the embodiment of using as the collection liquid the same alkanolamine or alkanolamide as the raw material.

DETAILED DESCRIPTION OF THE INVENTION

Figure 1:
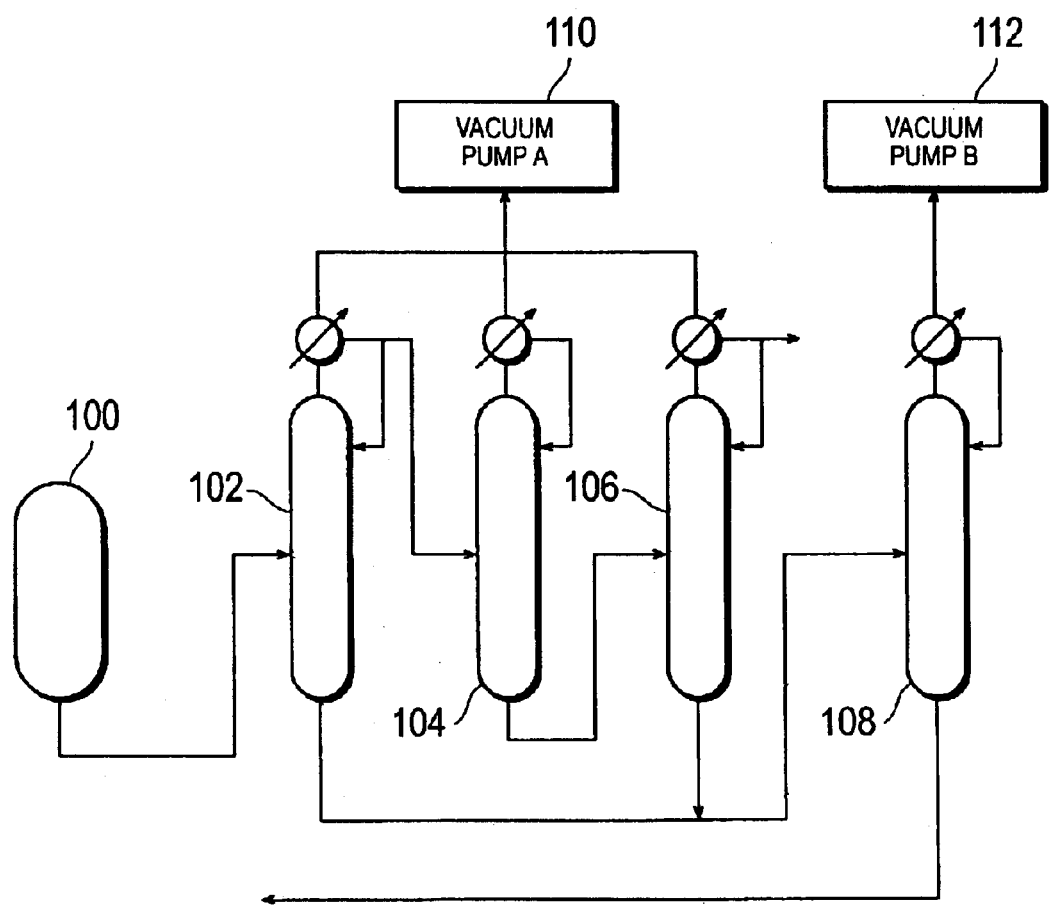
FIG. 1 is a system diagram illustrating a collecting step, purifying step, and recovering step contemplated by this invention.

As examples of the alkanolamine used in the present invention, monoethanol amine, iso-propanol amine, 2-amino-1-propanol, 1-amino-2-butanol, 2-amino-1-butanol, N-hydroxyethyl methylamine, N-hydroxyethyl ethylamine, N-hydroxyethyl piperidine, N-hydroxyethyl pyrrolidine, and N-hydroxyethyl morpholine may be cited. In this invention, such an alkanolamine is used as a starting raw material and is also used as a collecting agent for collecting the reaction gas, which results from the dehydrating reaction.

The aziridines obtained by subjecting the alkanolamines to the dehydrating reaction are respectively ethyleneimine, 2-methyl ethyleneimine, 2-ethyl ethyleneimine, N-methyl ethyleneimine, N-ethyl ethyleneimine, N-vinyl methylamine, N-vinyl ethylamine, N-vinyl piperidine, N-vinyl pyrrolidine, and N-vinyl morpholine.

The information regarding the alkanolamine and the aziridines may be referred to JP-A-04-217659 and U.S. Pat. No. 4,966,980.

As examples of the alkanolamide used in the present invention, N-hydroxyethyl acetamide, N-hydroxyethyl pyrrolidone, and N-hydroxyethyl caprolactam are cited. In this invention, such an alkanolamide is used as a starting material and as a collecting agent for collecting the reaction gas, which results from the dehydrating reaction.

Concrete examples of the N-vinyl amide obtained by the dehydrating reaction of alkanolamides, N-vinyl acetamide, N-vinyl pyrrolidone, and N-vinyl caprolactam are cited.

The conditions for producing aziridines or N-vinyl amides from alkanolamine or alkanolamide through the reaction step, collecting step and/or a condensation step, purifying step, and recovering step is not particularly restricted. The component steps are carried out under generally known conditions excepting the point that the vacuum distillations at the purifying step and the recovering step are effected with mutually different decompression systems. To be specific, the component steps are implemented as follows.

<Reaction Step>

An alkanolamine or an alkanolamide as a raw material is gasified with a vaporizer and then introduced into a reaction vessel packed with a catalyst. The dehydrating reaction of the raw material proceeds at a catalyst bed temperature in the range of 300–500° C., preferably 350–450° C. The pressure may be normal pressure, reduced pressure, or increased pressure. In the case of the reduced pressure, the reaction generally proceeds under a pressure in the range of 20–400 hPa.

The alkanolamine or alkanolamide as the raw material, when necessary, may be in the form diluted with such an inert gas as nitrogen or helium. The concentration of the alkanolamine or alkanolamide can be properly decided to suit the reaction conditions, for example. When the dehydrating reaction proceeds under the reduced pressure, it is recommendable to set the concentration of the alkanolamine or alkanolamide in the raw material gas at 90 vol. % or more. Generally, the dehydrating reaction is preferred to be carried out by using a raw material gas that is formed substantially solely of an alkanolamine or alkanolamide.

The space velocity of the feed gas cannot be generally specified because it is variable with the kind of a catalyst to be used, the reaction temperature, the reaction pressure, and the like. Nevertheless, the space velocity is generally in the range of 10–20,000 $hr^{-1}$ (STP), preferably 50–5000 $hr^{-1}$ (STP). When the dehydrating reaction proceeds under a reduced pressure, the space velocity is preferably in the range of 50–2000 $hr^{-1}$ (STP).

The reaction vessel to be used herein may be of the fixed bed flow type or the fluidized bed type.

The catalyst to be used for the dehydrating reaction may be any of the catalysts that are generally used for the dehydrating reaction of alkanolamines and alkanolamides. For example, the catalysts, which are disclosed in EP-0227461, EP-0228898, and EP-0230776, may be used. As concrete examples of the catalyst, the oxide compositions represented by the formula, $X_1 P_{0.01-3} Y_{0-100} O_m$ (wherein X denotes an alkali metal or alkaline earth metal, P denotes a phosphorus, Y denotes such an element as B, Al, Si, S, Sc, Ti, Cu, Y, Zr, Nb, Mo, or Sn, and m denotes a numeric value which is automatically determined by the numbers of the atoms of other elements) may be cited.

At the reaction step, when the raw material is an alkanolamine, such amines as ammonia, methyl amine, and ethyl amine and such carbonyl compounds as acetaldehyde and acetone are by-produced in addition to the aziridines as target products. Then, when the raw material is an alkanolamide, such amines as piperazine and alkyl piperazines, and aldehydes and ketones such as propion aldehyde, methylethyl ketone, and n-butyl aldehyde are by-produced in addition to the N-vinyl amides as target products.

The information regarding the dehydrating reaction of alkanolamines may be referred, for example, to JP-A-04-217659 and U.S. Pat. No. 4,966,980, for example.

<Collecting Step>

At the collecting step, the aziridines or the N-vinyl amides are collected by causing the reaction gas containing the aziridines or the N-vinyl amides, which is obtained in the reaction step, to contact an alkanolamine or an alkanolamide. At this time, the carbonyl compound in the reaction gas reacts with the alkanolamine to form Schiff bases and/or ketimines.

The collecting conditions are not particularly restricted. This collection may be implemented by following any of the generally known methods such as, for example, the methods disclosed in JP-A-04-217659 and U.S. Pat. No. 4,966,980.

<Condensation Step>

The condensation step may be adopted instead of the collection step. Optionally, both the collection step and the condensation step may be adopted. At the condensation step, the reaction gas containing aziridines or the N-vinyl, which is obtained in the reaction step, are cooled by a heat exchanger, for example, to be condensed. The condensation conditions are not particularly restricted. This condensation may be implemented by any of the generally known methods such as, for example, the methods disclosed in JP-B-05-55498.

<Purifying Step>

At the purifying step, the collection liquid obtained at the collecting step is subjected to vacuum distillation so as to separate amines. By this vacuum distillation, the aziridines or the N-vinyl amides as target products are purified.

The purifying conditions are not particularly restricted. This purification may be effected by following any of the generally known methods such as, for example, the methods disclosed in JP-A-04-217659 and U.S. Pat. No. 4,966,980. The method of vacuum distillation may be of either the batchwise type or the continuous type. Industrially, the continuous method of vacuum distillation proves advantageous.

The collection liquid obtained at the collecting step is supplied from a collecting column (100) to the first distillation column (102) as illustrated in FIG. 1, for example. By the vacuum distillation in the first distillation column (102), aziridines or N-vinyl amides are extracted together with amines through the top of the column. The unaltered alkanolamine or alkanolamide, Schiff bases or ketimines, the generated water, and other a heavy fraction are extracted as the bottoms of the column. Then, the top liquid of the first distillation column is supplied to a second distillation column (104). By the vacuum distillation in the second distillation column (104), amines are extracted through the top of the column. Meanwhile, aziridines or N-vinyl amides and the bottom liquid containing part of the unaltered raw material are extracted through the bottom of the column. The bottom liquid is further supplied to a third distillation column (106). By the vacuum distillation in the third distillation column (106), the aziridines or the N-vinyl amides as the target products are obtained through the top of the column. By the vacuum distillations performed in the first distillation column (102), the second distillation column (104), and the third distillation column (106), the amines and part of the target products are allowed to emanate as a vaporizing gas through vacuum lines. Preferably, for the purpose exalting the yields of aziridines or N-vinyl amides as target products, the alkanolamine or alkanolamide as the raw material is added to the supplied liquid directed toward the second distillation column (104) or the third distillation column (106), and the vacuum distillation is performed.

The purified aziridines or N-vinyl amides are obtained as described above. Though the embodiment using three distillation columns has been described, the number of distillation columns is not particularly restricted.

<Recovering Step>

At the recovering step, the bottom liquid from the purifying step is introduced into a distillation column (108) and subjected therein to vacuum distillation. In the case of the production of aziridines, for example, the Schiff base and the ketimines in the bottom liquid are decomposed and converted into alkanolamines and carbonyl compounds. Then, the carbonyl compounds are extracted through the top of the column. The alkanolamines are recovered through the bottom of the column. In the case that a collecting agent besides the alkanolamines is used for collection, the collecting agent is also recovered.

The bottom liquids of the first distillation column (102) and the third distillation column (106) are mixed and the mixture is supplied at a fourth distillation column (recovering column) (108) and subjected therein to vacuum distillation as illustrated in FIG. 1, for example. At this step of vacuum distillation, the Schiff bases and the ketimines are decomposed into carbonyl compounds and alkanolamines. Through the top of the column, the carbonyl compounds are extracted together with the generated water. Through the bottom of the column, the alkanolamines are extracted and recovered. Incidentally, by adding water to the bottom liquid before it is supplied to the fourth distillation column (108), the decomposition of the Schiff bases and the ketimines may be promoted. The alkanolamines extracted through the bottom of the column may be used in their unaltered form as the raw materials for the reaction. The alkanolamines may be further purified for the removal of a heavy fraction. Through the top of the fourth distillation column (108), part of the carbonyl compounds flow into the vacuum lines as the vaporizing gas.

At the purifying step, the distillation column of either the packed type or the plate type may be used. The distillation for purification may be performed by following any of the generally known methods such as the methods disclosed in JP-A-04-217659 and U.S. Pat. No. 4,966,980. The column top temperature is in the range of 10–100° C. and the pressure is in the range of 1–750 hPa, preferably 5–700 hPa.

This invention is characterized by performing the decompression at the purifying step and the decompression at the recovering step with mutually different decompression systems. In other words, the depression system of the purifying step and the depression system of the recovering step are mutually independent. The term "decompression system" as used herein embraces the vacuum pumps serving to maintain the distillation columns under a reduced pressure, the vacuum lines serving to connect the distillation columns to the vacuum pumps, and the devices such as pressure adjusting valves which are annexed thereto.

Specifically, in the embodiment illustrated in FIG. 1, the first distillation column (102), the second distillation column (104), and the third distillation column (106) and a vacuum pump A (110) are connected with vacuum lines. The first distillation column (102), the second distillation column (104), and the third distillation column (106) are decompressed with the vacuum pump A (110). The fourth distillation column (108) is connected to a vacuum pump B (112) through vacuum lines. The fourth distillation column (recovering column) (108) is decompressed with the vacuum pump B (112).

The decompression at the purifying step and the decompression at the recovering step are carried out with mutually different decompression system as described above, with the result that the amines from the purifying step will be prevented from being mixed with the carbonyl compounds, the aldehydes, and ketones from the recovering step. Consequently, these compounds are prevented from reacting with each other. Thus, the formation of a solid substance in the vacuum pumps and the vacuum lines is prevented.

EXAMPLES

Now, this invention will be described more specifically below with reference to working examples. The symbol "%" means "mass %" unless otherwise specified.

Example 1

The gas phase intramolecular dehydration of monoethanol amine by the use of a catalyst containing lithium and phosphorus [$Li_1P_{0.3}$ (atomic ratio, exclusive of oxygen)] and prepared in accordance with the procedure described in Example 1 of EP-0228898 was carried out under the following conditions.

Reaction temperature: 390° C.

Feed gas: Monoethanol amine, 100 vol. %

The reaction gas containing ethylene imine was collected with monoethanol amine. The collection liquid had the following composition.

0.91% of amines comprising ammonia, methyl amine, and ethyl amine; 0.01% of acetaldehyde; 22.05% of ethylene imine; 52.79% of monoethanol amine; 10.89% of water; 5.20% of Schiff base (formed by the reaction of monoethanol amine with acetaldehyde); and 8.15% of other substances.

Then, ethylene imine was purified and monoethanol amine was recovered by using a continuous vacuum distillation apparatus composed of four distillation columns (three ethylene imine purifying columns and one monoethanol amine recovering column) as illustrated in FIG. 1.

Specifically, the collection liquid was supplied at a rate of 2 kg/h to the intermediate stage of the first distillation column and subjected to vacuum distillation therein under the conditions of 400 hPa in pressure, 40° C. in column top temperature, and 110° C. in column bottom temperature. A liquid consisting of 95.82% of ethylene imine and 4.18% of light boiling amine fraction was extracted through the top of the column. Through the bottom of the column, a liquid composed of 68.55% of monoethanol amine, 14.15% of water, 6.76% of Schiff base, and 10.64% of other substances was extracted.

The column top liquid, by the addition of ethanol amine thereto, had the percentage composition thereof converted to 79.65% of ethylene imine, 17.86% of ethanol amine, and 2.49% of light boiling amine fraction. The resultant liquid was supplied to the intermediate stage of the second distillation column and subjected to vacuum distillation therein under the conditions of 760 hPa in pressure, 45° C. in column top temperature, and 60° C. in column bottom temperature. Through the top of the column, 100% light boiling amine fraction was extracted. Through the bottom of the column, a liquid consisting of 81.25% of ethylene imine, 17.86% of ethanol amine, and 0.89% of other amines was extracted.

Subsequently, the bottom liquid of the column was supplied to the intermediate stage of the third distillation column and subjected to vacuum distillation therein under the conditions of 400 hPa in pressure, 40° C. in column top temperature, and 130° C. in column bottom temperature. Ethylene imine, which has the purity of 99.80%, was obtained through the top of the column. The bottom liquid of the column was formed of monoethanol amine containing 2.30% of ethylene imine.

The bottom liquids of the first and the third distillation column were mixed and supplied to the intermediate stage of the fourth distillation column. The mixed bottom liquid consisted of 69.66% of monoethanol amine 13.2% of water, 6.31% of Schiff base, 0.15% of ethylene imine, and 10.67% of other substances. In the fourth distillation column, the vacuum evaporation was performed under the conditions of 200 hPa in pressure, 70° C. in column top temperature, and 130° C. of column bottom temperature. A liquid consisted of 18.01% of acetaldehyde, 1.00% of ethylene imine, 63.5% of water, and 17.94% of other substances was extracted through the top of the column. The bottom liquid of the column consisted of 88.08% of monoethanol amine, 0.83% of Schiff base, and 11.09% of other substances.

The vacuum lines issuing from the tops respectively of the first distillation column, the second distillation column, and the third distillation column were joined short of the entrance to the vacuum pump A and connected to the vacuum pump A. The vacuum line issuing from the top of the fourth distillation column was connected to the vacuum pump B. The distillation columns used at the purifying step and the recovering step were decompressed with mutually different decompression systems.

When the continuous distillation was performed for one month, the operation of distillation proceeded steadily without entailing either formation of a deposit in the vacuum lines or fluctuation of vacuum pressure.

Comparative Example 1

An operation of distillation was performed by following the procedure of Example 1 while using the vacuum pump A alone. The vacuum lines issuing respectively from the first distillation column, the second distillation column, the third distillation column, and the fourth distillation column were joined short of the entrance to the vacuum pump A and connected to the vacuum pump A.

Immediately after the start of the continuous distillation, the deposition of a solid substance on the inner walls of the vacuum lines short of the entrance to the vacuum pump A was confirmed. After the elapse of seven hours following the start of the distillation, the distillation could not be continued steadily because the vacuum pressure began to fluctuate. Thus, the operation was stopped and the vacuum lines and the vacuum pump were washed.

Example 2

The gas phase intramolecular dehydration of N-hydroxyethyl pyrrolidone by the use of the same catalyst as in Example 1 was carried out under the following conditions.

Reaction temperature: 390° C.

Feed gas: N-hydroxyethyl pyrrolidone 100 vol. %

The reaction gas containing N-vinyl pyrrolidone was collected with N-hydroxyethyl pyrrolidone. The collection liquid had the following composition.

0.91% of light boiling amines; 0.05% of acetaldehyde; 57.30% of N-vinyl pyrrolidone; 25.00% of N-hydroxyethyl pyrrolidone; 10.33% of water; 5.20% of Schiff base (formed by the reaction of the decomposed amine compounds with the aldehyde compounds); and 1.21% of other substances.

Then, the N-vinyl pyrrolidone was purified and the N-hydroxyethyl pirrolidone was recovered by using a continuous vacuum distillation apparatus composed of four distillation columns (three N-vinyl pyrrolidone purifying columns and one N-hydroxyethyl pyrrolidone recovering column) as illustrated in FIG. 1.

Specifically, the collection liquid was supplied at a rate of 1 kg/h to the intermediate stage of the first distillation column and subjected to vacuum distillation therein under the conditions of 133 hPa of pressure, 90° C. of column top temperature, and 150° C. of column bottom temperature. Through the top of the column, light boiling amines and N-vinyl pyrrolidone were extracted. Through the bottom of the column, N-hydroxyethyl pyrrolidone, Schiff base, and other heavy fraction were extracted.

The top liquid of the column was supplied to the intermediate stage of the second distillation column and subjected to vacuum distillation under the conditions of 66 hPa in pressure, 45° C. in column top temperature, and 60° in column bottom temperature. Through the top of the column, light boiling amines were extracted. Through the bottom of the column, a liquid formed of N-vinyl pyrrolidone and N-hydroxyethyl pyrrolidone was extracted.

Then, the bottom liquids of the first and the third distillation column were mixed and supplied to the intermediate stage of the fourth distillation column. In the fourth distillation column, the vacuum distillation was carried out under the conditions of 260 hPa in pressure, 70° C. in column top temperature, and 130° C. in column bottom temperature. Through the top of the column, a liquid consisted of 18.01% of acetaldehyde, 1.00% of N-vinyl pyrrolidone, 63.5% of water, and 17.94% of other substances was extracted. The bottom liquid of the column consisted of 88.08% of N-hydroxyethyl pyrrolidine, 0.83% of Schiff base, and 11.09% of other substances.

The vacuum lines issuing from the tops respectively of the first distillation column, the second distillation column, and the third distillation column were joined short of the entrance to the vacuum pump A and connected to the vacuum pump A. The vacuum line issuing from the top of the fourth distillation column was connected to the vacuum pump B. The purifying step and the recovering step were decompressed with mutually different decompression systems.

When the continuous distillation was performed for one month, the operation of distillation proceeded steadily without entailing either formation of a deposit in the vacuum lines or fluctuation of vacuum pressure.

What is claimed is:

1. A method for the production of aziridine, which comprises a reaction step for obtaining a reaction gas containing aziridine by the gas phase intramolecular dehydration of an alkanolamine, a collecting step for obtaining a collection liquid containing aziridine by causing the reaction gas to contact a collecting agent and/or a condensation step for obtaining a condensed liquid containing aziridine by cooling the reaction gas, a purifying step for obtaining purified aziridine by introducing the collection liquid and/or the condensed liquid into a distillation column and subjecting the collection liquid and/or the condensed liquid to vacuum distillation therein, and a recovering step for recovering the alkanolamine by introducing the bottom liquid in the distillation column at the purifying step into a distillation column and subjecting the bottom liquid to vacuum distillation therein, and the decompression at the purifying step and the decompression at the recovering step are carried out with mutually different decompression systems.

* * * * *